United States Patent [19]

Moy

[11] 4,329,512

[45] May 11, 1982

[54] PROCESS FOR PREPARING ACETALDEHYDE

[75] Inventor: David Moy, Ridgewood, N.J.

[73] Assignee: The Halcon SD Group, Inc., New York, N.Y.

[21] Appl. No.: 194,330

[22] Filed: Oct. 6, 1980

[51] Int. Cl.$^3$ .................. C07C 47/06; C07C 45/41
[52] U.S. Cl. .................. 568/484; 568/485; 568/486; 568/488
[58] Field of Search ............. 568/484, 485, 488, 486

[56] References Cited

U.S. PATENT DOCUMENTS

| | | | |
|---|---|---|---|
| 2,727,902 | 12/1955 | Reppe et al. ................. | 568/485 |
| 3,285,948 | 11/1966 | Butter ........................... | 568/485 |
| 3,356,734 | 12/1967 | Kuraishi et al. .............. | 568/485 |
| 3,531,531 | 9/1970 | Copelin ......................... | 568/484 |
| 3,579,566 | 5/1971 | Fenton .......................... | 568/485 |
| 3,631,188 | 12/1971 | Wakamatsu et al. .......... | 568/484 |

*Primary Examiner*—Werren B. Lone
*Attorney, Agent, or Firm*—William C. Long; David Dick; Riggs T. Stewart

[57] ABSTRACT

Acetaldehyde is produced by reacting acetic anhydride with hydrogen in the presence of a Group VIII noble metal catalyst wherein the reaction is carried out in the liquid phase but the reaction is maintained under boiling conditions and the entire reaction effluent is in vapor form.

4 Claims, No Drawings

PROCESS FOR PREPARING ACETALDEHYDE

This invention relates to the preparation of acetaldehyde and is more particularly concerned with the preparation of acetaldehyde by conversion of acetic anhydride.

Acetaldehyde is a well-known chemical of commerce, used primarily as an intermediate in the production of organic chemicals, and has been produced commercially for many years, for example by the hydration of acetylene and the catalytic oxidation of ethyl alcohol, ethylene and saturated hydrocarbons such as butane. More recently it has been discovered that acetaldehyde can be produced by the action of carbon monoxide and hydrogen upon alcohols, ethers and esters in the presence of catalysts based on metals of the 8th Group of the Periodic Table. Such reactions are described, for example, in Reppe et al. U.S. Pat. No. 2,727,902, Butter U.S. Pat. No. 3,285,948, Kuraishi et al. U.S. Pat. No. 3,356,734, and Japanese Patent publication 48-19286, and require the use of very high superatmospheric pressures. Belgian Pat. No. 839,321, which is the counterpart of U.S. application Ser. No. 654,662 filed Feb. 5, 1976, discloses the preparation of acetaldehyde as a by-product in the manufacture of ethylidene diacetate by reacting carbon monoxide and hydrogen with methyl acetate at moderate superatmospheric pressures. The selectivity to acetaldehyde described in these publications is, however, in general relatively low and this is obviously a disadvantage when acetaldehyde is the desired product. Fenton U.S. Pat. No. 3,579,566 treats organic acid anhydrides such as acetic anhydride with hydrogen in the presence of a catalyst comprising a complex of a Group VIII noble metal with a biphyllic ligand from the group consisting of trihydrocarbyl phosphines, arsines and stibines. The Fenton examples show the preparation primarily of ethylidene diacetate from acetic anhydride by this technique. Small amounts of acetaldehyde are also reported by Fenton but the amounts produced are inadequate when it is desired to have acetaldehyde as the principal product along with acetic acid. Belgian Pat. No. 879,178 converts anhydrides to 1,1-diesters with hydrogen in the presence of certain supported metals, including metals of Group VIII of the Periodic Table, and in the presence of a strong protonic acid such as hydrochloric and hydrofluoric acids. No formation of acetaldehyde is shown.

It is, therefore, an object of this invention to provide a process for the preparation of acetaldehyde in which the selectivity to acetaldehyde is significantly increased and in which the reaction can be carried out at moderately elevated pressures.

In accordance with this invention, this and other objects are realized by reacting acetic anhydride with hydrogen in the presence of a Group VIII noble metal catalyst in a boiling reaction zone, preferably by operating in a continuous manner with continuous feed of acetic anhydride as well as hydrogen to the boiling reaction zone. A boiling reaction zone is one which is operated under temperature and pressure conditions such that the reactants and products present are continuously boiling, i.e., they are being continuously vaporized and the reaction product effluent is removed from the reaction zone in the vapor state, as distinguished from conventional liquid phase reactions wherein the product effluent is withdrawn as a liquid stream. The boiling reaction zone is also distinguished from a vapor phase zone wherein the reactants and the reaction products are essentially all in the vapor phase at all times. It has been surprisingly discovered that when a Group VIII noble metal catalyst, especially palladium, rhodium, ruthenium and platinum, particularly palladium, is employed and the reaction is carried out in a boiling reaction zone of the character described, the selectivity to acetaldehyde is significantly increased and can approach its theoretical maximum, making possible increased yields.

The reaction of hydrogen upon acetic anhydride to produce acetaldehyde can be illustrated by the following equation:

$$CH_3\overset{O}{\overset{\|}{C}}O\overset{O}{\overset{\|}{C}}CH_3 + H_2 \longrightarrow CH_3CHO + CH_3COOH$$

As will be seen from the foregoing equation, one mol of acetic anhydride will theoretically produce a mol of acetaldehyde and a mol of acetic acid. In accordance with the invention, the formation of other products, such as ethylidene diacetate, which tend to reduce the yield of acetaldehyde is minimized so that the quantity of acetaldehyde produced from a unit quantity of acetic anhydride will more nearly approach the theoretical. At the same time, the amount of acetic anhydride converted to acetaldehyde and acetic acid is maintained at a desirable level. The term "selectivity" is used herein has its conventional meaning viz.

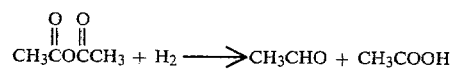

As will be seen from the equation set forth above, the theoretical selectivity to acetaldehyde is 100% when one mol of acetaldehyde and one mol of acetic acid are produced per mol of acetic anhydride reacted.

The Group VIII noble metal catalyst can be supplied and used in any convenient form, viz. in the zero valent state or in any higher valent form. For example, the catalyst may be the metal itself in finely-divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Preferably the Group VIII noble metal is used in the form of a salt or in the zero valent form. For this purpose, typical salts include palladium bromide ($PdBr_2$), palladium chloride ($PdCl_2$), palladium chloride dihydrate ($PdCl_2.2H_2O$), palladium trifluoride ($PdF_3$), palladium iodide ($PdI_2$), palladium nitrate ($Pd(NO_3)_2$), palladium sulfate ($PdSO_4.2H_2O$), palladium acetate, and the like. These illustrative forms are typical of the forms of the other Group VIII noble metals which can be used, e.g., rhodium chloride ($RhCl_3$), rhodium iodide ($RhI_3$), ruthenium chloride ($RuCl_3$), platinum bromide ($PtBr_2$), platinum chloride ($PtCl_3$), etc. When the catalyst is in zero valent form, it is preferably supported, i.e., it is dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst, or the catalyst mixture, followed by drying. If desired, the catalyst can be pre-activated, for example, by heating it in the presence of hydrogen. Catalyst component concentration upon the carrier may vary widely, e.g., 0.01 weight of percent to 10 weight percent, or higher.

The amount of Group VIII noble metal catalyst is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, the catalyst is employed in the amount of 1 mol per 50 to 5,000 mols of acetic anhydride, preferably 1 mol per 300 to 2,500 mols of acetic anhydride, most most preferably 1 mol per 1,000 to 2,000 mols.

The hydrogen is preferably employed in substantially pure form, particularly with respect to diluent gases, as available commercially, but inert diluents such as nitrogen, methane, and noble gases can be present if desired. The presence of inert diluents does not affect the reaction but their presence makes it necessary to increase the total pressure in order to maintain the desired hydrogen partial pressure. The hydrogen is preferably substantially free of CO. The hydrogen should also be essentially dry, i.e., the hydrogen and the other reactants should be reasonably free from water. The presence of minor amounts of water such as may be found in the commercial forms of the reactants is, however, entirely acceptable.

The process of this invention can be carried out in the presence of a solvent or diluent, if desired. The solvent or diluent can be any organic solvent which is inert in the environment of the process, but preferably there are used relatively high-boiling paraffinic hydrocarbons such as hexadecane and decalin, aromatic hydrocarbons such as biphenyl, phenanthrene, anthracene and tetralin, halogenated hydrocarbons such as chlorobenzenes, e.g., trichlorobenzene, or carboxylic acids, e.g., those containing up to 16 carbon atoms such as acetic acid, or relatively high-boiling esters and cellosolve acetate, and the like. Preferred solvents are trichlorobenzene, decalin, anthracene and tetralin. Mixtures of solvents can also be used. In general, high-boiling solvents have been found to be the most suitable for use when a solvent is employed in the process. A solvent or diluent is suitably selected which has a boiling point sufficiently different from the other components in the reaction mixture that it can readily be separated by distillation, as will be readily apparent to persons skilled in the art.

The temperature of the reaction mixture is selected to keep the reaction mixture under continuously boiling conditions, i.e., to maintain continuous vaporization of the liquid reaction mixture, at the total pressure and total gas flow rate employed. Ordinarily, the temperature will lie within the range of 100° and 225° C. Higher temperature can be employed but there is no particular advantage in their use. The time of reaction is not a parameter of the process and depends largely upon the temperature employed.

The feed of gas to the reaction zone, ie., hydrogen, and recycle gas, is suitably effected by directing the gas into the liquid boiling reaction medium so that the gas passes upwardly through it. This not only provides agitation but facilitates control of the partial pressure of the gas. The reaction is carried out under superatmospheric pressure but excessively high pressures, which require special high-pressure equipment, are not necessary. In general, the reaction is effectively carried out by employing a hydrogen partial pressure which is preferably 50 to 3,000 psi, although a hydrogen partial pressure within the broader range of 10 to 10,000 psi can also be employed. The total pressure is that required to provide the desired hydrogen partial pressure and that required to maintain the liquid phase but to allow boiling conditions. Typically, total pressures up to about 3,500 psig are used. The reaction can be advantageously carried out in an autoclave or similar apparatus.

It will be apparent that the reactions referred to above are carried out under substantially anhydrous conditions. The presence of minor amounts of water, however, such as may be found in commercially available reactants, is permissible. Normally, however, the presence of more than 5 mol % of water in any one or more of the reactants should be avoided, the presence of less than 3 mol % of water desired, and the presence of less than 1 mol % is preferred.

The effluent from the reaction zone is entirely gaseous, i.e., it is composed of the non-condensible gases in the reaction system, e.g., hydrogen, as well as vaporized organic compounds including the product acetaldehyde, unreacted acetic anhydride, acetic acid and solvent, if present.

The vaporized reaction mixture is continuously removed from the reaction zone and partially condensed to separate the higher boiling constituents and to provide a net product consisting of acetaldehyde which is separately condensed or otherwise recovered from the non-condensible gas component, e.g., hydrogen. As has been previously mentioned, the above-described reaction lends itself readily to continuous operation in which the reactants, e.g., acetic anydride and hydrogen, are continuously supplied to the reaction zone and, after removal of acetaldehyde as above-described, the other components of the vapor effluent, both gaseous and liquid, particularly unreacted acetic anhydride and hydrogen, are continuously recycled to the reaction zone. The relatively non-volatile catalyst remains in the reaction zone at all times and only the vaporous effluent is removed. A purge of the recycled gases may be taken in conventional manner to prevent the build-up of contaminating gases which may have been present in the hydrogen feed to the system such as nitrogen or may have been produced in the reaction itself.

The following examples will serve to provide a fuller understanding of the invention, but it is to be understood that they are given for illustrative purposes only, and are not to be construed as limitative of the invention. In the examples, percentages are on a molar basis, unless otherwise indicated.

EXAMPLE 1

In this example, a 200 ml magnetically-stirred, glass-lined Parr bomb is employed as the reaction vessel. The vessel is provided with a vapor draw-off line containing a pressure regulator which is set to maintain the pressure in the vessel at 100 psig at all times. The vessel is charged with 30 grams of acetic anhydride and 0.5 gram of palladium on charcoal (5% by weight) along with about 30 cc. of trichlorobenzene, is swept out with argon and pressurized to 100 psig with hydrogen. The reactor is then placed in an oil bath at room temperature and brought to 160° C. in about 10 minutes. Under these conditions, the reaction mixture boils and the evolved vapors are drawn off. At the same time, hydrogen is fed to the reactor at a rate (30 liters per hour) to make up for that withdrawn with the effluent and to maintain the indicated pressure. After 1 hour, the reaction is discontinued. During the reaction, the effluent is subjected to a first condensation to separate the portions of the effluent having higher boiling points than acetaldehyde and the acetaldehyde is then condensed to separate it from the non-condensible gas component. The ratio of acetaldehyde to acetic acid is found to be 0.33 and there is a yield of 25.8% of acetaldehyde. This example illustrates batch operation in which all of the acetic anhydride is initially charged.

EXAMPLE 2

Example 1 is repeated but the yield is carried out at a temperature of 185° C. The yield of acetaldehyde is found to be 63% and the ratio of acetaldehyde to acetic acid is 0.68.

COMPARATIVE EXAMPLE A

Example 2 is repeated except that about 0.25 cc. of orthophosphoric acid is added to the charge. The yield of acetaldehyde is found to fall to only 5% and the ratio of acetaldehyde to acetic acid is only <0.1. Most of the acetic anhydride is found to have been converted to ethylidene diacetate. This example illustrates the adverse effect upon acetaldehyde formation of strong protonic acids.

Example 3

In this example and in the following examples, the process of the invention is carried out with a continuous supply of reactants. Using a reactor as described in Example 1, the vessel is initially charged with the catalyst which is supported and is 0.5 gram of palladium on activated carbon (5% weight) along with about 30 cc. of trichlorobenzene, is swept out with argon and pressured to 100 psig with hydrogen. The reactor is then brought up to 185° C. in about 10 minutes and as soon as the reaction mixture begins to boil, a continuous feed of acetic anhydride is begun at the rate of 20 cc. per hour and hydrogen is continuously introduced at the rate of 20 liters per hour. The reaction is continued at 100 psig for 1.5 hours. Acetaldehyde is recovered as described in Example 1 and is found to have been produced in 57% yield with an acetaldehyde to acetic acid ratio of 0.74.

EXAMPLE 4

Example 3 is repeated but the reaction pressure is reduced to 60 psig, the acetic anhydride feed rate is 18.7 cc. per hour and the hydrogen feed rate is 40 liters per hour. After a reaction period of one hour, the yield of acetaldehyde is found to be 63% and the ratio of acetaldehyde to acetic acid is 0.64.

EXAMPLE 5

Example 4 is repeated except that the acetic anhydride feed rate is reduced to 12.4 cc. per hour and the reaction time is increased to 2 hours. Acetaldehyde is produced in a yield of 70% with an acetaldehyde to acetic acid ratio of 1.

EXAMPLE 6

The process of Example 3 is repeated except that the amount of 5% of palladium on activated carbon is increased to 1.1 grams and the hydrogen feed rate is increased to 40 liters per hour. After 1.25 hours of reaction, it is found that the yield of acetaldehyde is 80% and the ratio of acetaldehyde to acetic acid is 1. In a further embodiment carried out for 1.33 hours with an acetic acid feed rate of 18.8 cc. per hour, there is realized an acetaldehyde yield of 70% and an acetaldehyde to acetic acid ratio of 1.

EXAMPLE 7

Using the apparatus and procedure described in Example 3, the reaction was carried out in the presence of a catalyst in the form of 0.7 gram of palladium chloride at a temperature of 185° C., a hydrogen pressure of 100 psi, an acetic anhydride feed rate of 17.6 cc. per hour and a hydrogen feed rate of 77 liters per hour. After 1.42 hours of reaction, the yield of acetaldehyde is found to be 57% and the acetaldehyde to acetic acid ratio is determined to be 0.89.

COMPARATIVE EXAMPLE B

Example 4 is repeated but in the presence of the 0.25 cc. of ortho-phosphoric acid. After 1.32 hours of reaction, it is found that the yield of acetaldehyde is only 16%. The ratio of acetaldehyde to acetic acid is 0.51.

COMPARATIVE EXAMPLE C

Example 7 is repeated using 2 grams of palladium chloride plus 1 cc. orthophosphoric acid. In this case, the yield dropped dramatically to 1% and the ratio of acetaldehyde to acetic acid is less than 0.1.

What is claimed is:

1. A process for the preparation of acetaldehyde which comprises reacting acetic anhydride with hydrogen in the presence of a Group VIII noble metal catalyst wherein the reaction is carried out in the liquid phase but the reaction mixture is maintained under boiling conditions and the entire reaction effluent is in vapor form.

2. A process as defined in claim 1, wherein the reaction is carried out under a pressure of 100° C. to 225° C. and under a partial pressure of hydrogen of 50 to 300 psi.

3. A process as defined in claim 1, wherein the Group VIII noble metal is palladium.

4. A process as defined in claim 3, wherein the palladium catalyst is palladium in zero valent state on a support.

* * * * *

UNITED STATES PATENT AND TRADEMARK OFFICE
CERTIFICATE OF CORRECTION

PATENT NO. : 4,329,512
DATED : May 11, 1982
INVENTOR(S) : David Moy

It is certified that error appears in the above-identified patent and that said Letters Patent is hereby corrected as shown below:

Col. 2, line 29 - "is" should be --as--

Col. 3, line 1 - delete "of"

Col. 5, line 35 - "(5% weight)" should be --5% by weight--

Col. 6, line 12 - "embodiment" should be --experiment--

Col. 6, line 20 - "tbe" should be --the--

Signed and Sealed this

Twenty-third Day of August 1983

[SEAL]

Attest:

GERALD J. MOSSINGHOFF

Attesting Officer    Commissioner of Patents and Trademarks